United States Patent [19]

Itatani et al.

[11] 4,042,603

[45] Aug. 16, 1977

[54] INTRAMOLECULAR CYCLIZATION IN A FATTY ACID ESTER SOLVENT

[75] Inventors: Hiroshi Itatani; Mikito Kashima; Akinori Shiotani; Hataaki Yoshimoto; Tetuo Kato, all of Ichihara, Japan

[73] Assignee: UBE Industries, Ltd., Ube, Japan

[21] Appl. No.: 559,065

[22] Filed: Mar. 17, 1975

[30] Foreign Application Priority Data

Mar. 29, 1974   Japan .................................. 49-34618

[51] Int. Cl.$^2$ .......................................... C07D 307/91
[52] U.S. Cl. ........................... 260/346.71; 260/465 R; 260/465 D; 260/465 F; 260/465 G; 260/465 H; 260/471 R; 260/473 F; 260/475 R; 260/479 R; 260/590 FB
[58] Field of Search ................... 260/479 R, 346.2 M, 260/591 FB, 465 H, 475 R

[56] References Cited

PUBLICATIONS

Yoshimoto et al., Bulletin of the Chemical Society of Japan, vol. 46, (Aug. 1973), pp. 2490–2492.
House, Modern Synthetic Reactions, W. A. Benjamin, Inc., New York, (1965), pp. 294–295.
Shiotani et al., Angew. Chem. (July 1974), vol. 86 (13), pp. 478–479.

Primary Examiner—Henry R. Jiles
Assistant Examiner—Bernard Dentz
Attorney, Agent, or Firm—Flynn & Frishauf

[57] ABSTRACT

A process for preparing substituted dibenzofuran or fluorenone-9 by the intramolecular cyclization of substituted diphenyl ether or benzophenone in the presence of a carboxylic acid salt of palladium and/or palladium organic complex.

20 Claims, No Drawings

INTRAMOLECULAR CYCLIZATION IN A FATTY ACID ESTER SOLVENT

This invention relates to a process for preparing heterocyclic compounds. More particularly, this invention is to provide a process for preparing heterocyclic compounds having the formula (2):

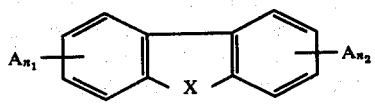

wherein
A represents an alkyl, alkoxy, nitro, halogen, alkanoyloxy, alkoxycarbonyl, phenyl and substituted alkyl radical which is substituted with alkoxy, nitro, halogen, alkoxycarbonyl, phenyl or nitrile and $n_1$ and $n_2$ are zero or an integer of 1–4 and $n_1 + n_2$ are integers of 1–8 and X represents oxygen or carbonyl which comprises intramolecular-cyclizing the compounds having the formula (1):

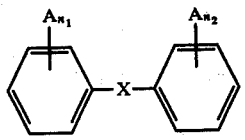

wherein
A, $n_1$, $n_2$ and X have the same meanings as above and the above compound has at least two hydrogen atoms at both 2-and 2'-positions, under pressure of an oxygen-containing atmosphere in the presence of carboxylic acid salts of palladium and/or palladium organic complexes as catalysts and the reaction scheme is represented by the formula (3) as follows:

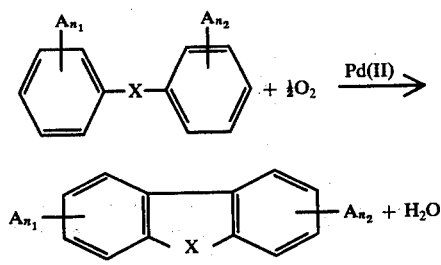

wherein
A, $n_1$, $n_2$ and X have the same meanings as above.

As to preparation of dibenzofuran, there have heretofore been known a method of preparing it by diazocoupling orthoaminodiphenylether and condensing the resultant product (J. Org. Chem. Soc., 26 4749 (1961), and a method for preparing it by dehydrating 2,2'-dihydroxybiphenyl (Acta Chimica Scan., 22 681 (1968)).

As to preparation of 9-fluorenone, there have been known several methods: a method of thermal decomposition of diphenic acid (J. Am. Chem. Soc., 53 2720 (1931)); a method of preparing it from benzoic acid anhydride in the presence of a rhodium catalyst (J. Org. Chem., 34, 3076, (1969), ibid, 34 3233 (1970)), and a method of preparing it by oxydation of fluorene (C.A. 73 120400j).

But these known methods give not only poor yields of these compounds, but also need several stages. More particularly, benzofuran derivatives and 9-fluorenone derivatives having substituents cannot be obtained by these methods.

Diphenyl ether can give heterocyclic compounds, that is, benzofuran under thermal intramolecular cyclization:

But in the case of substituted diphenyl ethers, substituted benzofurans could not be obtained only by thermolysis at 700° C.

Therefore, we studied the useful preparation of heterocyclic compounds (2) which are substituted and have found that the compounds having the formula:

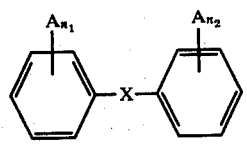

wherein the positions at both 2- and 2'-positions are not substituted and
A, $n_1$ and $n_2$ have the same meanings as above, are caused to react under pressure of oxygen-containing atmosphere in the presence of a carboxylic acid salt of palladium and/or a palladium organic complex to give easily the compounds with substituents in aromatic ring having the formula (2):

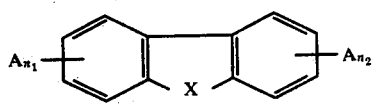

wherein
A, $n_1$ and $n_2$ have the same meanings as above, in one step.

The substituted aromatic compounds having the formula (1) used for this invention as starting materials need have hydrogen atoms at both 2- and 2'-positions and in the case of having the substituents at such positions, it is impossible to obtain the desired hetero aromatic compounds. That is, in the case of having substituents in any other positions than 2- and 2'-positions, this invention can be carried out regardless of the positions, numbers of substituents and characters of X connecting aromatic rings.

The substituents, as was explained in formula (2) represent alkyl, alkoxy, nitro, halogen, alkanoyloxy, alkoxycarbonyl, phenyl and substituted alkyl radicals which are substituted with alkoxy, nitro, halogen, alkoxycarbonyl, phenyl or nitrile radical. These radicals, as was shown in the above scheme (3), does not directly participate in the reaction. X in the above formula (1) as starting material means oxygen or carbonyl, and this invention is carried out under any choice of X regardless of the kinds, numbers of the above substituents.

As the representative compounds of the above formula (1) as starting material, there can be following compounds: 4,4'-dimethyldiphenyl ether, 3,4'-dimethyldiphenyl ether, 3,3'-dimethyldiphenyl ether, 2,4'-dimethyldiphenyl ether, 2,2'-dimethyldiphenyl ether, 4-methyldiphenyl ether, 3-methyldiphenyl ether, 2-ethyldiphenyl ether, 4,4'-diethyldiphenyl ether, 3,3'-diethyldiphenyl ether, 3,4'-diethyldiphenyl ether, 2,2'-diethyldiphenyl ether, 4,4'-dimethoxydiphenyl ether, 3,4'-dimethoxydiphenyl ether, 2,2'-dimethoxydiphenyl ether, 4,4'-diethoxydiphenyl ether, 2,2'-diethoxydiphenyl ether, 3,4'-diethoxydiphenyl ether, 3,3'-diethoxydiphenyl ether, 4-methoxydiphenyl ether, 3-methoxydiphenyl ether, 2-methoxydiphenyl ether, 4-ethoxydiphenyl ether, 3-ethoxydiphenyl ether, 2-ethoxydiphenyl ether, 4-nitrodiphenyl ether, 3-nitrodiphenyl ether, 2-nitrodiphenyl ether, 4,4'-dinitrodiphenyl ether, 3,4'-dinitrodiphenyl ether, 3,3'-dinitrodiphenyl ether, 2,2'-dinitrodiphenyl ether, 2,4'-dinitrodiphenyl ether, 4,4'-difluorodiphenyl ether, 4,4'-dibromodiphenyl ether, 4,4'-dichlorodiphenyl ether, 3,4'-difluorodiphenyl ether, 3,4'-dibromodiphenyl ether, 3,4'-dichlorodiphenyl ether, 3,3'-difluorodiphenyl ether, 3,3'-dichlorodiphenyl ether, 3,3'-dibromodiphenyl ether, 2,4'-dibromodiphenyl ether, 2,4'-dichlorodiphenyl ether, 2,4'-difluorodiphenyl ether, 4-methyl-4'-chlorodiphenyl ether, 4-methoxy-4'-chlorodiphenyl ether, 4-ethoxy-4'chlorodiphenyl ether, 4-methyl-4'-bromodiphenyl ether, methyl 4-phenoxybenzoate, methyl 3-phenoxy benzoate, 4,4' dimethoxycarbonyldiphenyl ether, 4,4'-di(1,2-dibromoethyl)-diphenyl ether, 4(1,2-dibromoethylphenyl)-phenyl ether, 4,4'-di(1-bromoethyl)-diphenyl ether, 4(2-acetoxyethylphenyl)phenyl ether, 4(2-nitroethylphenyl)-phenyl ether, 4(2-cyanoethylphenyl)phenyl ether, 1,4-(di-p-tolyloxy)benzene, bis(4-phenoxyphenyl)ether, 4,4'-phenoxyphenyl)ether, 4,4'-dimethylbenzophenone, 4,4'-diethylbenzophenone, 2-methylbenzophenone, 4-methylbenzophenone, 4,4'-dimethoxybenzophenone, 4,4'-diethoxybenzophenone, 2,2'-dimethoxybenzophenone, 4-nitrobenzophenone, 4,4'-dinitrobenzophenone, 4-chlorobenzophenone, 4-fluorobenzophenone, 4-methoxycarbonylbenzophenone, 4,4'-dimethoxycarbonylbenzophenone, 4-acetoxydiphenyl ether, bis(α-chloroparatolyl) ether, bis(α-bromoparatolyl) ether, bis(α,α-dichloro-α-phenylparatolyl) ether, bis(3,5-diphenoxyphenyl) ether, 2,4-dichlorophenylparanitrophenyl ether, p-chlorophenyl p-dodecylphenyl ethyl, p-nitrophenyl p-tolyl ether, phenyl α-phenyltolyl ether, bis(α-phenyl-p-tolyl) ether, 3,5-diisopropylphenyl phenyl ether, 2,4-dinitrophenyl p-xylyl ether bis(α-xylyl-p-tolyl) ether, o-chlorophenyl p-nitrophenyl ether, 2-nitro-p-tolylphenyl ether, 4-biphenylphenyl ether, 3-biphenyl m-chlorophenyl ether, and p-fluorophenyl p-nitrophenyl ether.

As to catalysts used for this invention, carboxylic acid salts of palladium and palladium organic complexes are preferable. These useful palladium compounds can easily produce a redox system with substituted aromatic compounds as starting materials under pressure of oxygen-containing atmosphere:

Pd(II) + 2RH + ½O₂ → Pd(O) + R − R + H₂O

Pd(O) + RH + O₂ → R − PdOOH

R − PdOOH + RH → R − R + Pd(O) + HOOH

But it is difficult for inorganic palladium salts such as palladium chloride to form a redox system under pressure of oxygen, so that they are not favorable.

As to carboxylic acid salts of palladium, either a fatty acid salt and an aromatic acid salt are favorable, but the former is preferred. As to fatty acid salts, salts of fatty acids having 1–5 carbon atoms such as palladium formate, palladium acetate, palladium propionate, palladium butyrate, and palladium valerate are preferred. As to aromatic carboxylic acid salts, there can be mentioned palladium phthalate, palladium benzoate and the like.

As to palladium organic complexes, there can be mentioned, for example; acetylacetone palladium complex, benzoylacetone palladium complex, propionylacetone palladium complex, butyrylacetone palladium complex, dibenzoylmethane palladium complex, isobutyrylacetone palladium complex, caproylacetone palladium complex, tetraacetylethane palladium complex, dibenzylidene palladium, and bisbenzonitrile palladium. These palladium organic complexes act as the same excellent catalysts as the above fatty acid salts.

An amount of the catalyst used for this reaction is of the range $$\frac{1}{10} \sim \frac{1}{1000} \text{ mole, preferably } \frac{1}{50} \sim \frac{1}{1000} \text{ mole}$$

per substituted aromatic compound (1).

On carrying out this invention, in cases where, for example, diketones such as acetylacetone, benzoylacetone, difluoroacetylacetone, 3-chloroacetylacetone, hexafluoroacetylacetone, β-ketoacid ester such as ethyl acetoacetate, methyl acetoacetate, methyl trifluoroacetoacetate or β-ketoacid such as acetoacetic acid, propionylacetic acid, all of which are components of palladium organic complexes are added to the reaction system together with catalysts as promotors, the yields can be increased in comparison with the case in which the above components are not added. The amount added of the β-diketone, β-ketoacid ester or β-ketoacid is preferably 0.5 − 4 moles to the catalyst.

Also, the reaction can be carried out in the absence of solvents, but the use of solvents can prohibit side-reaction and promote intramolecular cyclization, so that it is preferable to use solvents.

As to solvents, any organic solvent which does not react with the starting materials under reaction conditions, that is, aromatic compounds having the formula (4):

(4)

wherein
Z represents an alkyl, alkoxyl, alkoxycarbonyl and alkanoyloxy radical, $n_3$ represents an integer of 2–6, or fatty acid esters are preferable.

As to representative solvents, there can be mentioned, for example, aromatic compounds such as mesitylene, pseudocumene, p-xylene, 1,2-dimethyl-4-methoxybenzene, trimethyl trimellitate, methyl 3,5-dimethylbenzoate, tetramethyl pyromellitate, 1,4-diacetoxybenzene, 1,2,4-triacetoxybenzene, fatty acid esters such as butyl acetate, methyl valerate, ethyl butyrate, ethylene glycol diacetate, ethylene glycol monomethylether acetate, ethylene glycol monoethylether acetate, dimethyl malonate and the like.

It is very important to carry out the reaction of this invention under pressure of an oxygen-containing atmosphere. It does not proceed under normal pressure. Even if it is carried out under pressure, it does not proceed without an oxygen-containing atmosphere. Only under pressure of an oxygen-containing atmosphere, that is, by adding oxygen under pressure to the reaction system, the above carboxylic acid salt of palladium and palladium organic complexes can be endowed with catalytic activity so that intromolecular cyclization can be carried out.

The pressure is 2–300 kg/cm², preferably 5–40 kg/cm² of oxygen partial pressure. In cases where the oxygen partial pressure is below 2 kg/cm², the reaction almost does not proceed and even in the case of above 300 kg/cm² the yields of heterocyclic compounds are not much different from the case of the said pressure and so the use of such high pressure is not economical. In cases where the reaction is carried out under pressure of an oxygen-containing atmosphere, the oxygen used may be pure oxygen, but in this case there is danger of explosion. Therefore, it is generally economical to use oxygen gas which is diluted with inert gas such as nitrogen gas or carbon dioxide gas.

The reaction temperature is generally 20°–300° C, preferably 100°–200° C.

the intramolecular cyclization of this invention proceeds with the reaction time to give the desired heterocyclic compounds. But a long reaction time increases the amount of by-product formed, so that the reaction time is generally 0.5 –8 hours, preferably 1–6 hours.

The main side reaction is a dehydrogenating dimerization reaction. For example, 4,4'-dimethyldiphenyl ether produces the dimer (in this case, three kinds of dimers) besides the desired 2,8-dimethylbenzofuran as shown in the next reaction scheme (5):

cult to prepare, can be easily prepared and many new heterocyclic compounds have been prepared.

The compounds obtained according to this invention are used as plasticizers, cross linking agents of plastics, and intermediate of mordants, agricultural chemicals and medicinals. Particularly, the dicarboxylic acids obtained by oxidation of the dimethyl heterocyclic compounds according to this invention can be used as polyesters and polyamides for fiber and plastics and the diamino heterocyclic compounds obtained by reduction of dinitro derivatives according to this invention are used as polyesters and polyamides for fiber and plastics.

This invention is illustrated by the following examples, but these are not meant to limit the scope of the invention.

EXAMPLE 1

15 g of 4,4'-dimethyldiphenyl ether, 0.034 g (0.15 m. mole) of palladium acetate and 0.015 g (0.15 m. mole) of acetylacetone were placed in a glass vessel and this is placed in a 100 ml-autoclave. Then a mixture gas of nitrogen and oxygen of molar ratio 1:1 was filled in it to 50 kg/cm² of inner pressure. The autoclave was shaken at 150° C for 5 hours. After completion of the reaction, the reaction mixture was subjected to fractional distillation. After distilling out the unreacted 4,4'-dimethyldiphenyl ether, a distillate having b.p. 130°–135° C/12 mmHg was recrystallized from ethanol to give 2.6 g (13 m. moles) of 2,8-dimethyldibenzofuran. The obtained 2,8-dimethylbenzofuran showed m.p. 62°–64° C (reference value, 64° C).

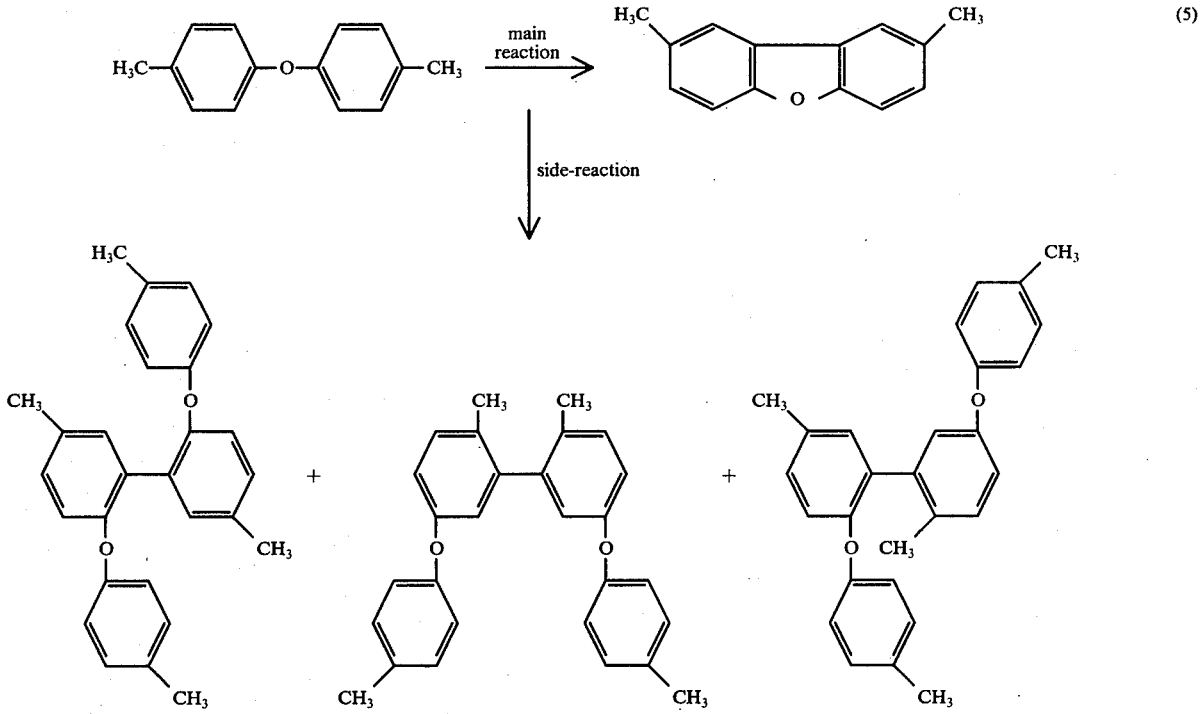

This invention can be carried out batchwise, continuously, and semicontinuously. The heterocyclic compounds, products of this invention, can be recovered from the reaction mixture by a known method such as evaporation, distillation or filtration and purified by a known method such as recrystallization.

According to this invention, heterocyclic compounds having several substituents which are heretofore difficult to prepare, can be easily prepared and many new Elementary analysis for $C_{14}H_{12}O$ (%):
Found: C, 85.33; H, 6.23. Calculated: C 85.68; H,6.17.
NMR spectrum (CCl₄) δ : ppm
2.48, Me (S) 6H
6.98–7.74, ph (m) 6H
Mass spectrum m/e = 196 (parent peak)
The results of these analysis confirmed that the obtained product was 2,8-dimethylbenzofuran.

From the higher boiling point part of the above reaction mixture was obtined a dimer of dimethyldiphenyl ether which has a Mass spectrum m/e = 394 and the following elementary analysis for $C_{28}H_{26}O_2$: Found; C = 84.94 %, H = 6.33 %; Calculated C = 85.25 %, H = 6.64 %. Gas chromatography showed that the dimer weighed 0.87 g (2.2 m. moles).

EXAMPLE 2

By treating 4,4'-dimethyldiphenyl ether under the same reaction conditions as in Example 1 except that 15 ml of mesitylene was added as solvent, 2.7 g of 2,8-dimethylbenzofuran (14 m. moles) was obtained and 0.79 g (2.0 m. moles) of the dimer also obtained.

EXAMPLE 3

By treating 4,4'-dimethyldiphenyl ether under the same reaction conditions as in Example 2 except that acetylacetone was not added, 1.3 g (6.8 m. moles) of 2.8-dimethyldibenzofuran was obtained and 0.36 g (0.9 m. mole) of the dimer also obtained.

EXAMPLE 4

This example was carried out under the same conditions as in Example 1 except that 15.0 g of 4,4'-dimethyldiphenyl ether, 0.038 g (0.15 m. mole) of palladium propionate, 0.015 g (0.15 m. mole) of acetylacetone and 5 ml of ethylene glycol diacetate were employed. As a result, 2.78 g (14 m. moles) of 2,8-dimethyldibenzofuran and 0.78 g (2.0 m. moles) of the dimer also obtained.

EXAMPLE 5

This example was carried out under the same reaction conditions as in Example 1 except that 29.0 g of 4,4'-dimethyldiphenyl ether, 0.067 g (0.30 m. mole) of palladium acetate, and 0.030 g of acetylacetone (0.30 m. mole) were employed and the mixture was reacted for 7 hours. As a result, 5.9 g (30 m. moles) of 2,8-dimethyldibenzofuran was obtained and 1.9 g (4.7 m. moles) of the dimer also obtained.

EXAMPLE 6

By treating 3,4'-dimethyldiphenyl ether under the same conditions as in Example 1 except that 15.0g of 3,4'-dimethyldiphenyl ether was used instead of 4,4'-dimethyldiphenyl ether, 0.22 g (1.1 m. moles) of 2,7-dimethyldibenzofuran and 0.35 g (0.89 m. mole) of the dimer were obtained.

EXAMPLE 7

By treating 3,4'-dimethyldiphenyl ether under the same conditions as in Example 6 except that 5 ml of ethylene diacetate was added, 2.7 g (14 m. moles) of 2,7-dimethyldibenzofuran and 0.27 g (0.69 m. mole) of the dimer were obtained. The obtained 2,7-dimethyldibenzofuran melted at 82°–83° C and was in the form of white needle crystals.

Elementary analysis for $C_{14}H_{12}O$ (%): Found: C, 85.54; H, 6.24. Calaculated: C, 85.68; H, 6.17.

NMR spectrum ($CCl_4$) δ : ppm
2.48, (S) 6H, Me
6.92–7.78, (m) 6H, ph
Mass spectrum m/e = 196 (parent peak)

The above results comfirmed that the product is 2,7-dimethylbenzofuran.

EXAMPLE 8

By treating 3,4'-dimethyldiphenyl ether under the same conditions as in Example 7 except that the mixed gas pressure of nitrogen and oxygen (molar ratio 1:1) was changed to 20 kg/cm², 2.2 g (11 m. moles) of 2,7-dimethyldibenzofuran and 0.25 g (0.63 m. mole) of the dimer were obtained.

EXAMPLE 9

By treating 4,4'-dimethylbenzophenone under the same conditions as in Example 1 except that 15.0 g of 4,4'-dimethylbenzophenone was used and the reaction temperature was changed to 180° C, and by subjecting the reaction mixture to gas chromatography, 0.31 g (1.7 m. moles) of 3,6-dimethylfluorenone-9 was obtained. Traces of the dimer were obtained.

EXAMPLE 10

By treating 4,4'-dimethyldiphenyl ether under the same conditions as in Example 1 except that acetylacetone was not added. 1.2 g (6.1 m. moles) of 2,8-dimethylbenzofuran and 0.36 g (0.9 m. mole) of the dimer were obtained.

EXAMPLES 11–19

15.0 g of the starting material described in Table 1, 0.15 m. mole of organic palladium compound, 0.015 g (0.15 m. mole) of acetylacetone and 5 ml of ethylene glycol diacetate were placed in a glass vessel and charged in a autoclave. The autoclave was filled with nitrogen and oxygen (molar ratio 1:1) to 50 kg/cm² of inner pressure and shaken at 150° C for 5 hours. After completion of the reaction, the reaction mixture was subjected to gas chromatography and preparative gas chromatography to identify and determine quantitatively the formed heterocyclic compounds and dimers.

Table 1

| Example No. | Organic palladium compound | Starting material | Yield Heterocyclic compound | Dimer |
|---|---|---|---|---|
| 11 | Palladium acetate 0.034 g | 4,4'-dimethoxydiphenyl ether  H₃CO—⟨⟩—O—⟨⟩—OCH₃ | 2,8-dimethoxydibenzofuran  H₃CO  OCH₃  2.7 g (12 m. moles) | 0.46 g (3.4 m. moles) |
| 12 | Palladium propionate 0.038 g | 4-nitrodiphenyl ether  ⟨⟩—O—⟨⟩—NO₂  1.7 g (8 m. moles) | 2-nitrodibenzofuran  NO₂ | 0.21 g (0.5 m. mole) |

Table 1-continued

| Example No. | Organic palladium compound | Starting material | Yield Heterocyclic compound | Dimer |
|---|---|---|---|---|
| 13 | Palladium acetate 0.034 g | 4-methoxycarbonyl-diphenyl ether | 2-methoxycarbonyl-dibenzofuran 2.1 g (9.1 m. moles) | 1.8 g (3.9 m. moles) |
| 14 | Acetylacetate palladium (II) 0.046 g | 4,4'-dichlorodiphenyl ether | 2,8-dichlorodibenzofuran 0.24 g (1.0 m. mole) | 0.14 g (0.3 m. mole) |
| 15 | Palladium acetate 0.034 g | 4-nitrobenzophenone | 3-nitrofluorenone-9 0.20 g (0.9 m. mole) | 0.18 g (0.4 m. mole) |
| 16 | Palladium acetate 0.034 g | 4,4'-dichlorobenzo-phenone | 3,6-dichlorofluorenone-9 0.1 g (0.4 m. mole) | 0.04 g (0.08 m. mole) |
| 17 | Palladium benzoate 0.052 g | 4,4'-diphenyldiphenyl ether | 2,8-diphenyldibenzo-furan 2.7 g (3.4 m. moles) | 3.1 g (4.8 m. moles) |
| 18 | Palladium acetate 0.034 g | Bis(α-chloro-p-tolyl) ether | 2,8-dichloromethyl-dibenzofuran 1.4 g (5.2 m. moles) | 0.1 g (0.18 m. mole) |
| 19 | Palladium acetate 0.034 g | 4-acetoxydiphenyl ether | 2-acetoxybenzofuran 1.8 g (9 m. moles) | 0.53 g (1.2 m. moles) |

What is claimed is:

1. A process for preparing a compound having the formula:

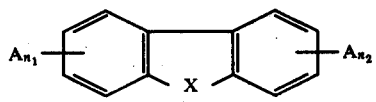

(2)

wherein
A represents an alkyl, alkoxyl, nitro, halogen, alkanoyloxy, alkoxycarbonyl, phenyl or alkyl radical which is substituted with alkoxy, nitro, halogen, alkoxycarbonyl, phenyl or nitrile radical, $n_1$ and $n_2$ are zero or an integer from 1 to 4, and $n_1 + n_2$ is an integer from 1 to 8; and X represents oxygen or carbonyl, which comprises contacting a substituted aromatic compound having the formula

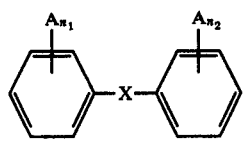

(1)

wherein
A, $n_1$, $n_2$ and X have the same meanings as above and the above compound has at least two hydrogen atoms at both the 2- and 2'-positions with at least one of a carboxylic acid salt of palladium and a palladium organic complex as a catalyst under pressure of an oxygen-containing atmosphere and in a fatty acid ester solvent whereby said compound (1) is cyclized intramolecularly.

2. The process as claimed in claim 1 wherein the fatty acid ester is selected from the group consisting of butyl acetate, ethylene glycol diacetate, ethylene glycol monoethyl ether acetate, and dimethyl malonate.

3. The process as claimed in claim 1 wherein a promotor is used.

4. The process as claimed in claim 3 wherein the promotor is selected from the group consisting of acetylacetone, hexafluoroacetylacetone, ethyl acetoacetate, and acetoacetic acid.

5. The process as claimed in claim 1 wherein the reaction is carried out under a partial pressure of 2–300 kg/cm$^2$ of oxygen.

6. The process as claimed in claim 5 wherein the reaction is carried out under a partial pressure of 5–40 kg/cm$^2$ of oxygen.

7. A process as claimed in claim 1 wherein the reaction is carried out at a temperature of 20°–300° C.

8. The process as claimed in claim 7 wherein the reaction is carried out at a temperature of 100°–200° C.

9. The process as claimed in claim 1 wherein the reaction is carried out for 30 minutes to 8 hours.

10. The proccess as claimed in claim 1 wherein the catalyst is a fatty acid salt of palladium having from 1 to 5 carbon atoms.

11. The process as claimed in claim 10, wherein the catalyst is a fatty acid salt of palladium selected from the group consisting of palladium formate, palladium acetate, palladium propionate, palladium butyrate and palladium valerate.

12. The process of claim 1, wherein the catalyst is a palladium organic complex.

13. The process as claimed in claim 12 wherein the palladium organic complex is selected from the group consisting of acetylacetone palladium complex, benzyolacetone palladium complex, propionylacetone palladium complex, butyrylacetone palladium complex, dibenzoylmethane palladium complex, isobutyrylacetone palladium complex, caproylacetone palladium complex, tetraacetylethane palladium complex, dibenzylideneacetone palladium and diphenylisocyanate palladium.

14. The process as claimed in claim 1 wherein the catalyst is palladium phthalate or palladium benzoate.

15. The process as claimed in claim 1 wherein the amount of the catalyst is from 0.1 to 0.001 mole per substituted aromatic compound (1).

16. A process as claimed in claim 1 wherein the solvent is ethylene glycol diacetate.

17. A process as claimed in claim 1 wherein A represents and alkyl group, each of $n_1$ and $n_2$ is 1, and X is oxygen.

18. A process as claimed in claim 1 wherein A represents methyl, each of $n_1$ and $n_2$ is 1, and X is oxygen.

19. A process as claimed in claim 1 wherein the substituted aromatic compound (1) is 3,4'-dimethyldiphenyl ether and the heterocyclic compound (2) is 2,7-dimethyldibenzofuran.

20. A process as claimed in claim 1 wherein the substituted aromatic compound (1) is 3,3'-dimethyldiphenyl ether and the heterocyclic compound (2) is 3,7-dimethyldibenzofuran.

* * * * *

UNITED STATES PATENT AND TRADEMARK OFFICE
CERTIFICATE OF CORRECTION

PATENT NO. : 4,042,603
DATED : August 16, 1977
INVENTOR(S) : HIROSHI ITATANI et al It is certified that error appears in the above—identified patent and that said Letters Patent are hereby corrected as shown below:

Column 3, line 21: replace "4-ethoxy-4'chlorodiphenyl" with --- 4-ethoxy-4'-chlorodiphenyl ---.

Column 3, line 44: after "ether" (second occurrence), insert a comma.

Column 3, lines 29-30: delete "4,4'-phenoxyphenyl)ether"

Column 5, line 18: after "with", insert --- an ---.

Column 5, line 22: replace "the" with --- The ---.

Column 7, line 2: replace "obtined" with --- obtained ---.

Column 12, line 21, Claim 17: replace "and" with --- an ---.

Signed and Sealed this

Fourth Day of April 1978

[SEAL]

Attest:

RUTH C. MASON
Attesting Officer

LUTRELLE F. PARKER
Acting Commissioner of Patents and Trademarks